United States Patent [19]

Ramsay et al.

[11] Patent Number: 5,034,542
[45] Date of Patent: Jul. 23, 1991

[54] PREPARATION OF MACROLIDE COMPOUNDS

[75] Inventors: Michael V. J. Ramsay, South Harrow; Derek R. Sutherland, Buckinghamshire; John B. Ward, Hertfordshire; Neil Porter, Pinner; Hazel M. Noble, Aylesbury; Richard A. Fletton, Ruislip; David Noble, Aylesbury, all of England

[73] Assignee: American Cyanamid Company, Stamford, Conn.

[21] Appl. No.: 363,765

[22] Filed: Jun. 9, 1989

[30] Foreign Application Priority Data

Jun. 10, 1988 [GB] United Kingdom ........... 8813760

[51] Int. Cl.$^5$ .................................... C07D 493/22
[52] U.S. Cl. .................................... 549/264
[58] Field of Search .................... 549/264; 514/450

[56] References Cited

FOREIGN PATENT DOCUMENTS

| 0001689 | 5/1979 | European Pat. Off. | 549/264 |
|---------|--------|--------------------|---------|
| 2166436 | 5/1986 | United Kingdom | 549/264 |
| 2176182 | 12/1986 | United Kingdom | 549/264 |
| 0215654 | 3/1987 | United Kingdom | 549/264 |

Primary Examiner—Richard L. Raymond
Assistant Examiner—Mark W. Russell
Attorney, Agent, or Firm—Bacon & Thomas

[57] ABSTRACT

A process for the preparation of a compound of formula (I)

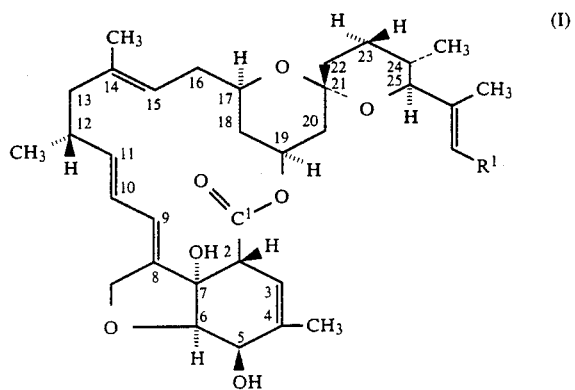

(in which $R^1$ is methyl, ethyl or isopropyl) by hydrogenation of a corresponding compound having a double bond at the 22,23-position, for example in the presence of a rhodium catalyst.

11 Claims, No Drawings

PREPARATION OF MACROLIDE COMPOUNDS

This invention relates to a novel process for the preparation of antibiotic compounds.

The compounds of formula (I)

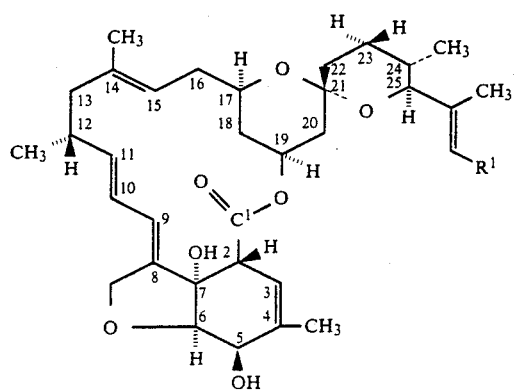

(in which R¹ is a methyl, ethyl or isopropyl group) are described in UK Patent Specification 2176182. These compounds have antibiotic activity and are useful in combating parasites in animals and humans and pests in agriculture, horticulture, forestry, public health and stored products. The compounds may also be used as intermediates in the preparation of other active compounds.

The present invention provides a novel and useful process for the preparation of compounds of formula (I) which comprises hydrogenating a compound of formula (II)

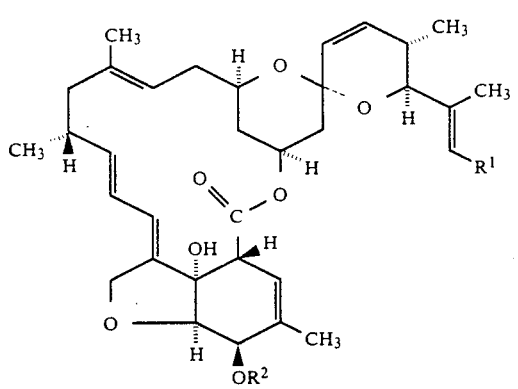

(in which R¹ is as defined above and R² is a hydrogen atom or a protecting group having up to 25 carbon atoms) followed, if necessary, by removal of the 5-OH protecting group.

Examples of groups serving as hydroxyl protecting groups are well-known and are described, for example, in "Protective Groups in Organic Synthesis" by Theodora W. Greene (Wiley-Interscience, New York 1981) and "Protective Groups in Organic Chemistry" by J. F. W. McOmie (Plenum Press, London, 1973). Examples of suitable protecting groups include acyl groups such as acetyl.

It will be appreciated that the compounds of formula (II) contain a number of reducible sites, and according to the present invention we described a method of reducing the 22,23-double bond without affecting the rest of the molecule.

The process according to the present invention is carried out under a hydrogen atmosphere in the presence of a homogeneous or heterogeneous catalyst suitable for the selective hydrogenation of the 22,23-double bond. Such catalysts include for example transition metal catalysts, e.g. a rhodium catalyst such as [(R³)₃P]₃RhX (where R³ is C₁₋₆ alkyl or phenyl optionally substituted by a C₁₋₄ alkyl group and X is a halogen atom). A preferred homogeneous catalyst for the reaction is tris(triphenylphosphine) rhodium (I) chloride.

The hydrogenation reaction takes place at a pressure of 1-4 atmospheres and conveniently in the presence of a solvent. Suitable solvents for the reaction include aromatic hydrocarbons such as benzene or toluene, alkanols e.g. ethanol, ethers e.g. tetrahydrofuran or esters e.g. ethyl acetate.

The hydrogenation reaction may be carried out at temperatures within the range of from room temperature to 100° C. and conveniently at room temperature.

When OR² is a protected hydroxyl group, removal of the protecting group may be effected by conventional methods, for example, those extensively described in the aforementioned textbooks of McOmie and Greene. Thus, for example, an acyl group such as an acetyl group may be removed by basic hydrolysis, e.g. using sodium or potassium hydroxide or ammonia is an aqueous alcohol such as methanol or by acidic hydrolysis, e.g. using concentrated sulphuric acid in ethanol.

A preferred embodiment of this process involves hydrogenating a compound of formula (II) (in which R¹ is an isopropyl group and R² is as defined above) followed, if necessary, by removal of the 5-OH protecting group to give a compound of formula (I) in which R¹ is an isopropyl group.

The compounds of formula (II) may be prepared from compounds of formula (III)

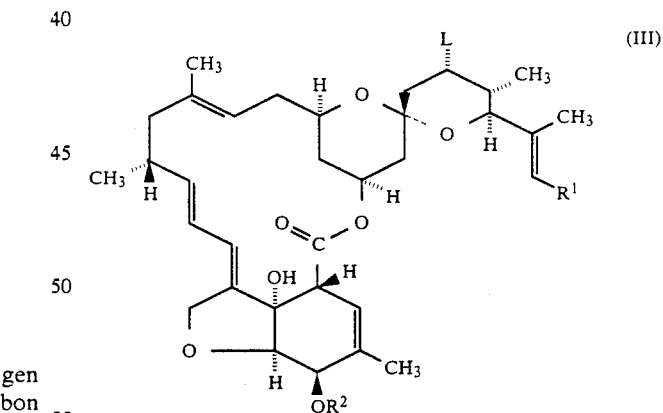

[where L is an eliminatable group, such as an acyloxy group e.g. PhOC(=S)O— or

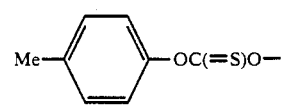

and R¹ and R² are as defined above in formula (II)].

The elimination reaction to yield the compounds of formula (II) may be effected by pyrolysis, for example at a temperature of 150° to 300° C., preferably 200° to 250° C., either in a suitable solvent such as a halogenated hydrocarbon e.g. trichlorobenzene or in the absence of a solvent using an inert diluent such as sand.

The intermediates of formula (III) wherein $R^2$ is hydrogen and L is a hydroxy group are described in UK Patent Specification No. 2166436A. The intermediate of formula (III) wherein $R^1$ is isopropyl, $R^2$ is hydrogen and L is a hydroxyl group shall hereinafter be referred to as 'Factor A'.

Intermediates of formula (III) in which L is an acyloxy group and/or $R^2$ is an acyl (e.g. acetyl) protecting group may be prepared from the corresponding 5-OH, 23-OH compounds by standard acylation procedures. Thus, acylation may be effected using an appropriate acid or a reactive derivative thereof, such as an acid halide (e.g. acid chloride), anhydride or activated ester. In preparing compounds of formula (III) in which $R^2$ is hydrogen it will be necessary to perform the acylation reaction on a 5-OH protected derivative followed by deprotection to provide the desired compound of formula (III).

The invention is illustrated but not limited by the following preparations and examples in which temperatures are in °C.

PREPARATION 1

5-Acetoxy Factor A

Factor A (3.0 g) in pyridine (20 ml) at $-5°$ was treated with acetic anhydride (8 ml) and the resulting solution left at 3° for 20 hr. Benzene (100 ml) was added and the solution concentrated in vacuo. The residual oil was chromatographed over silica using dichloromethane:acetone (40:1) as eluent to give the 5-acetate of Factor A (2.06 g), containing the 5,23-diacetate (10%). The compounds were separated by reverse-phase preparative hplc to give the title compound (79% recovery), $\lambda_{max}$ (EtOH 244.5 nm ($E_1^1$ 462), $\delta$(CDCl$_3$) includes 2.14 (s; 3H), m/z includes 654, 594 and 576.

PREPARATION 2

5-Acetoxy, 23-phenyloxythiocarbonyloxy Factor A

Phenyl chlorothionoformate (1.90 ml) was added to a stirred solution of the product of Preparation 1 (3.0 g) and pyridine (3.70 ml) in dichloromethane (30 ml) at room temperature, under an atmosphere of nitrogen. After stirring for 16 h the dark brown reaction mixture was diluted with ethyl acetate (250 ml), washed with 2M hydrochloric acid (2×250 ml), saturated sodium bicarbonate solution (250 ml) and brine (250 ml), and dried (Na$_2$SO$_4$). The solvent was evaporated and the residue purified by flash chromatography (250 g silica gel, Merck 9385). Elution with ethyl acetate:light petroleum (1:4→1:3) afforded the title compound as an orange foam (2.68 g) $\lambda_{max}$ (EtOH) 235.6 nm ($\epsilon$34,500), 243.4 nm ($\epsilon$36,200); $\nu_{max}$ 3470 (OH), 1730, 1710 cm$^{-1}$ (esters); $\delta$(CDCl$_3$) values include 7.42 (2H,t, J 8 Hz), 7.29 (1H,t,J 8 Hz), 7.12 (2H,d, J 8 Hz) 4.97 (1H,m), 3.96 (1H,d,J 10 Hz), 3.34 (1H,m) 2.17 (3H,s), 1.38 (1H,t,J 12 Hz).

PREPARATION 3

5-Acetoxy 23-desoxy $\Delta^{22}$ Factor A

A solution of the product of Preparation 2 (1.00 g) in dry diglyme (75 ml) was heated at reflux for 17 h under an atmosphere of nitrogen. On cooling the majority of the diglyme was removed by evaporation (bath temp 50°/1 mm Hg) and the residue dissolved in ethyl acetate (250 ml). The organic solution was washed with saturated sodium bicarbonate solution water and brine and dried (Na$_2$SO$_4$). The solvent was evaporated and the residue purified by flash chromatography (100 g silica gel, Merck 9385). Elution with ethyl acetate:light petroleum (1:4) afforded the title compound (730 mg) as a white foam, $[\alpha]_D^{21}$ +113° (c, 0.3, CHCl$_3$), $\lambda_{max}$ EtOH 245 nm ($\epsilon_{max}$ 30,000); $\nu_{max}$ (CHBr$_3$) 3460 (broad OH), 1235, 1730 and 1710 cm$^{-1}$ (ester); $\delta$(CDCl$_3$) include 0.84 (d, 6 Hz; 3H), 0.96 (d, 6 Hz; 3H), 0.99 (d, 7 Hz; 3H), 1.02 (d, 6 Hz; 3H), 1.52 (s; 3H), 1.66 (s; 3H), 1.74 (s; 3H), 2.15 (s; 3H) 3.33 (m; 1H), 3.71 (d, 10 Hz; 1H), 3.90 (s; 1H), 4.06 (d, 6 Hz; 1H), 5.52 (m; 2H) 5.56 (dd, 10 and 2 Hz; 1H). m/z=636 (M+).

EXAMPLE 1

5-Acetoxy, 23-desoxy Factor A

A solution of the product of Preparation 3 (40 mg) and tris (triphenylphosphine) rhodium chloride (17 mg) in dry toluene (3 ml) was stirred under a positive pressure of hydrogen for 72 h. Another portion of catalyst (32 mg) was added. After a further 7 h the solution was evaporated to leave a brown residue which, as a solution in hexane:ethyl acetate (2:1), was filtered through a short column of Merck Kieselgel 60, 70-230 mesh silica (5 g) made up in the same solvent system. The crude material so obtained was purified by reverse phase preparative HPLC to give the title compound as an off-white foam, (7 mg) $\nu_{max}$ (CHBr$_3$) 3420+3340 (OH), 1732 (acetate), 1710 cm$^{-1}$ (carbonyl); $\delta$(CDCl$_3$) includes 0.68 (d,5 Hz,3H), 2.16 (s,3H), 3.32 (m,1H).

EXAMPLE 2

23-Desoxy Factor A

A solution of the product of Example 1 (2.300 g) in methanol (57.5 ml) was cooled to 0.5°, treated dropwise with aqueous sodium hydroxide (150 mg) and the resulting yellow solution stirred for 3 h. The solution was diluted with dichloromethane (200 ml), washed with 2N-hydrochloric acid, water, brine, then dried (magnesium sulphate) and solvent was evaporated to give a yellow foam, which was then chromatographed on silica (Merck Kieselgel 60, particle size 0.063–0.200 mm, 70-230 mesh (200 g) eluting with hexane-ethyl acetate (3:1), affording the title compound as a white foam (1.81 g), $[\alpha]_D^{22}$ +143° (c 0.3, chloroform), $\delta$(CDCl$_3$) include 3.27 (m;1H), 3.42 (d9; 1H), 3.54 (m;1H) and 4.29 (t6; 1H), m/z include 596, 578, 560, 468, 450, 356, 314, 299, 249, 248, 221 and 151.

We claim:

1. A process for the preparation of a compound of formula (I)

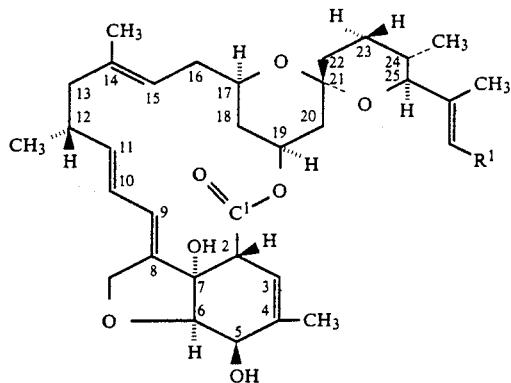

in which R¹ is a methyl, ethyl or isopropyl group; which comprises hydrogenating in the presence of a rhodium catalyst of the formula $[(R^3)_3P]_3RhX$, where $R^3$ is a $C_{1-6}$ alkyl or phenyl optionally substituted by a $C_{1-4}$ alkyl group and X is a halogen atom, a compound of formula (II)

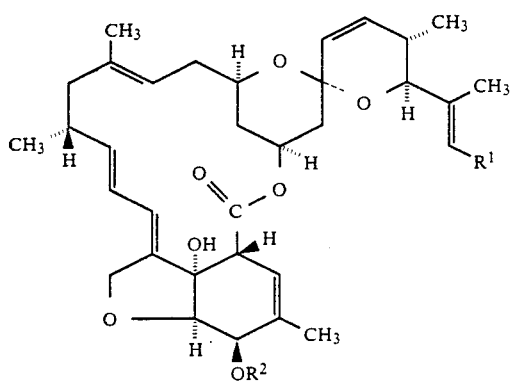

in which R¹ is as defined above and R² is a hydrogen atom or a protecting group having up to 25 carbon atoms, followed, if necessary, by removal of the 5-OH protecting group.

2. A process according to claim 1 in which the catalyst is tris(triphenylphosphine) rhodium (I) chloride.

3. A process according to claim 1 in which R² is an acetyl group.

4. A process according to claim 1 in which R¹ is an isopropyl group.

5. A process according to claim 1 in which the compound of formula (II) is prepared from a compound of formula (III)

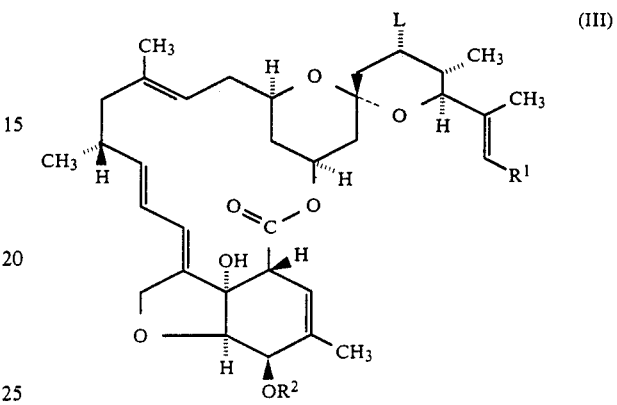

where L is an eliminatable group by elimination of the group L.

6. A process according to claim 5 in which L is a phenoxy- or p-tolyloxy-thiocarbonyloxy group.

7. A process according to claim 5 in which said elimination is effected by pyrolysis.

8. A process according to claim 7 in which L is an acyloxy group and the compound of formula (III) is prepared by acylation of a corresponding compound in which L is a hydroxyl group.

9. A process according to claim 6 in which said elimination is effected by pyrolysis.

10. A process according to claim 6 in which L is an acyloxy group and the compound of formula (III) is prepared by acylation of a corresponding compound in which L is a hydroxyl group.

11. A process according to claim 7 which L is an acyloxy group and the compound of formula (III) is prepared by acylation of a corresponding compound in which L is a hydroxyl group.

* * * * *